United States Patent [19]

Lambert

[11] Patent Number: 5,164,299

[45] Date of Patent: Nov. 17, 1992

[54] USE OF A MIXTURE OF CONJUGATED AND UNCONJUGATED SOLID PHASE BINDING REAGENT TO ENHANCE THE PERFORMANCE OF ASSAYS

[75] Inventor: Stephen B. Lambert, Rising Sun, Md.

[73] Assignee: E. I. Du Pont de Nemours and Company, Wilmington, Del.

[21] Appl. No.: 497,062

[22] Filed: Mar. 20, 1990

[51] Int. Cl.[5] .................... C12Q 1/00; G01N 33/53; G01N 33/566; G01N 33/544

[52] U.S. Cl. .................... 435/7.92; 435/7.93; 435/7.94; 435/7.95; 435/7.1; 436/501; 436/528; 436/532; 436/533; 436/534

[58] Field of Search .................. 435/7.1, 6, 7.92, 7.93, 435/7.94, 7.92, 4; 436/501, 528, 532, 819, 533, 534

[56] References Cited

U.S. PATENT DOCUMENTS 4,818,688 4/1989 Adamich et al. .................... 435/7

FOREIGN PATENT DOCUMENTS 0282192 9/1988 European Pat. Off. .

OTHER PUBLICATIONS

Skurrie et al., (1983) Enzyme Linked Immunosorbent Assay for Rubella . . . J. Clin. Microbiol. 17:738–743.
Geerligs et al. (1988) The influence of pH and ionic strength . . . J. Immuno Meth 106:239–244.
Jitsukawa et al., (1989) Increased coating efficiency of antigens . . . J Immuno Meth 116:251–257.
Yolken, R. H., *Reviews of Infectious Disease*, vol. 4, pp. 35–68, 1982.
McCullough, K. C., et al., *Journal of Immunological Methods*, vol. 82, pp. 91–100, 1985.
Geerligs, H. J., et al., *Journal of Immunological Methods*, vol. 106, pp. 239–240, 1988.
Brennand, D. M., *Journal of Immunological Methods*, vol. 93, pp. 9–14, 1986.

*Primary Examiner*—Christine M. Nucker
*Assistant Examiner*—David R. Preston

[57] ABSTRACT

In a solid phase homogeneous or heterogeneous assay for detection or quantitation of an analyte in a biological fluid, use of a combination of unconjugated binding reagent and carrier-conjugated binding reagent immobilized on the solid phase provides enhanced assay performance.

15 Claims, No Drawings

USE OF A MIXTURE OF CONJUGATED AND UNCONJUGATED SOLID PHASE BINDING REAGENT TO ENHANCE THE PERFORMANCE OF ASSAYS

TECHNICAL FIELD

This invention relates to the detection or quantitation of analytes in a biological fluid.

BACKGROUND

The performance of an immunoassay in the detection of a specified analyte is expressed in terms of sensitivity and specificity. The former is a measure of the test to correctly identify the samples in a population that are positive for the analyte. The latter is a measure of the test to correctly identify samples in a population that do not contain the analyte.

Immunoassay performance may be adversely affected by a number of interfering factors. Alleviation of these interferences may be effected by methods that are directed toward their cause. For example, as is described by Yolken (Yolken, R. H., 1982, Rev. Infec. Dis., 4:35-68) and is well established in the art, certain generic additives to assay reagents tend to improve the performance of the assay. Detergents such as Triton X-100 and proteins such as bovine serum albumin (BSA) reduce nonspecific protein-protein interactions and, thus, minimize non-immunochemical reactivities. Also, chelating agents such as ethylenediaminetetraacetate (EDTA) may increase the efficiency of added detergents and minimize complement-mediated phenomena, thereby improving immunoassay performance. Changes in assay performance brought about by the present invention were shown to be additional to the effects of detergents, nonspecific proteins and chelating agents.

Certain substances may be involved in specific but undesirable reactivities that occur within the chemistry of an immunoassay. Improvements in assay performance brought about by this invention do not rely upon the addition or subtraction of any new chemical or antigen. In an ELISA using a single, unconjugated antigen, the solid phase would already be coated with antigen and blocked with BSA. It is not obvious that replacement of a portion of the unconjugated antigen with BSA-conjugated antigen would constitute a chemical change in the character of the solid phase.

Some antigens may undergo changes in conformation, and therefore changes in reactivity, as a result of binding to carriers or solid surfaces (McCullough, K. C., Crowther, J. R. and Butcher, R. N., 1985, J. Immunol. Meth., 82:91-100). This phenomenon has been shown to be responsible for differences in sensitivity and specificity between immunoassay formats using the same reagents. Also, pH and ionic strength have been shown to affect the solid phase adsorption characteristics of proteins (Geerligs, H. J. et al., 1988, J. Immunol. Meth., 106:239-244). These factors would not be expected to be of importance in assays where highly specific binding partners are utilized as the binding and detection reagents. In the specific situation where one of the binding partners is a monoclonal antibody, a change in the conformation of an antigen to which the antibody is highly reactive would be expected to result in decreased rather than increased assay performance.

The chemistry by which reagents are bound to a solid phase may affect the performance of the resulting assay. Solid phase preparation protocols include passive, chemical, biochemical, immunologic (Brennand, D. M., Danson, M. J. and Hough, D. W., 1986, J. Immunol. Meth., 93:9-14) and covalent (Geerligs, H. J. et al., 1988) binding methods.

Certain antigens do not bind well to certain solid phase materials. It is not uncommon to conjugate those antigens to a carrier reagent such as, but not limited to, hemocyanin (Geerligs, H. J. et al., 1988) or BSA (Skurrie, I. J. and Gilbert, G. L., 1983, J. Clin. Microbiol., 17, 738-43) that will enhance their immobilization. This tends to increase the sensitivity of the subsequent assay by providing a solid phase that has more antigen available for reactivity with an incoming antibody. Other proteins such as ovalbumin, gelatin, casein, to name a few, can also be used as carriers. The improvement in assay performance that is brought about with the use of this invention relies upon a combination of conjugated and unconjugated antigen forms. Sensitivity and specificity are compromised by the use of either antigen form alone.

Jitsukawa et al., 1989, (Jitsukawa, T., Nakajima, S., Sugawara, I., and Watanabe, H., 1989, J. Immunol. Meth., 116:251-7) report an improvement in assay performance as a result of simultaneously binding a physical mixture of antigen and BSA or other "effector protein" to immunoassay plates. These authors state specifically that the observed results were due to independent binding of the two agents to the solid phase and not to each other. Their method is a one step coating and blocking procedure and does not result in the creation of a solid phase that is fundamentally different from those of established protocols.

A competition immunoassay for the detection of antibody directed against hepatitis B core antigen (HBcAg) has been described (Adamich, M. and Wos, S. M., U.S. Pat. No. 4,818,688, Apr. 4, 1989), incorporated here by reference. This assay format, using a high-affinity monoclonal antibody and purified, unconjugated antigen, is the state of the art technology over which the improvements comprising the present invention are based.

SUMMARY OF THE INVENTION

A combination of unconjugated and carrier-conjugated forms of one member of a pair of binding reagents is used in the preparation of the solid phase component of an assay that can then be used to detect and quantify an analyte. The other member of the pair of binding reagents can be the analyte or a reagent which selectively binds the analyte. The invention is applicable to various assay formats can be used, including but not limited to sandwich, inhibition, agglutination, and inhibition of agglutination formats. Binding pairs of reagents are exemplified by, but not limited to, antigen-antiantigen antibody, antigen-antiantigen antibody fragments, Protein A-IgG, lectin-polysaccharide, folate-folate binding protein, avidin-biotin, thyroxine-thyroxine binding globulin, steroid-steroid binding protein, intrinsic factor-B12, drug-drug receptor, polynucleotide segment-complementary polynucleotide segment, etc. Specific binding pairs used can be antibodies, receptors, lectins, or any other specific means of binding the analytes. The use of binding ligands which are reversibly bound to a receptor, for example biotin and avidin, antibody to fluorescein and fluorescein, can also be used with the mixture of conjugated and unconjugated binding reagent of this invention. The use of the mixture of conjugated and unconjugated reagent immobilized on the solid phase provides improved performance over that obtained with conjugated or unconjugated binding reagent alone.

DETAILED DESCRIPTION OF THE INVENTION

It is contemplated that the present invention may be applied to the detection of many different types of analytes for which there are specific binding partners. The analyte to be measured is usually a protein, peptide, antibody, carbohydrate, steroid, glycoprotein, nucleic acid or other molecule for which a specific binding partner can be isolated from a biological system or which can be synthesized. The analyte usually is selected from the group consisting of antigens and antibodies thereto; haptens and antibodies thereto; and hormones, vitamins, genetic material, metabolites and pharmacological agents and their receptors and binding partners. In particular, the methods of this invention are particularly well suited to the detection of antibodies which occur in response to exposure or infection with an etiological agent. Representative of such agents are the causative agents of hepatitis infections, such as hepatitis viruses A, B and C (non-A non-B), and retroviruses, herpes viruses, bacteria, fungi, chlamydia, rickettsia, and mycoplasma.

The binding reagent can be composed of any specific reagents, including purified naturally occurring proteins, polypeptides produced by recombinant means or enzymatic digestion of proteins, and synthetic peptides, as well as naturally occurring, recombinant or synthetic nucleic acids or carbohydrates. The binding reagent can be, for example, antigens or antibodies or antigen-binding antibody fragments (Fab, Fab', F(ab')2), lectins, carbohydrates, Protein A, or a member of a non-immune reversible binding pair, such as avidin-biotin, intrinsic factor-B12, T3-TBG, and folate-folate binding protein.

By carrier we mean a substance that is non-reactive in the analysis for the specific analyte, that bears functional groups permitting the analyte to be chemically linked to it, and that can be chemically bonded or physically adsorbed to a solid surface, thereby providing the reagent herein referred to as the solid-phase binding reagent. Carriers commonly used include albumins, globulins and hemocyanins, all of which can be obtained from many sources. Other suitable carriers include gelatin, casein and a variety of other peptides and proteins from synthetic or natural sources; polynucleotides, synthetic or purified from natural sources; linear or crosslinked polysaccharides; and various synthetic polymers not included in the categories mentioned.

Conjugation

By conjugation we mean the process of covalently attaching an analyte to a carrier. Numerous reagents and procedures for conjugating molecules are known and can be used in making conjugates for use in this invention. Molecules to be conjugated, here analyte and carrier, typically contain one or more of one or more of the following functional groups which can be used for conjugation: thiol groups, amino groups, carboxyl groups, and hydroxyl groups, phosphate groups or sulfo groups. However, if appropriate functional groups are lacking, they may be introduced by methods well known to the art.

Two molecules functionalized with thiol groups may be conjugated by oxidizing the thiols to disulfides. Alternatively, such molecules may be conjugated by linking the thiols with a homobifunctional reagent, such as a bis-maleimide or a bishaloacetyl compound. Two molecules functionalized with amine groups can be conjugated by use of homobifunctional reagents such as glutaraldehyde or disuccinimidyl esters. However, better control of a conjugation process may often be attained by utilizing a heterobifunctional reagent. For example, a molecule functionalized with thiol groups can be conjugated to a molecule functionalized with amine groups by means of a heterobifunctional reagent that possesses both maleimide and succinimidyl ester functions. Examples of heterobifunctional linkers include succinimidyl 4-(N-maleimidomethyl) cyclohexane-1-carboxylate (SMCC), succinimidyl 4-(iodoacetyl)aminobenzoate (SIAB) and succinimidyl 4-p maleimidophenyl) butyrate.

An additional means of conjugating molecules entails as a first step converting carboxyl groups, on one of the molecules to be conjugated, to a so-called active esters. The active esters can then react spontaneously with other functional groups, typically amines, on the other molecule of the desired conjugate pair. Although there are many reagents that convert carboxyl groups to active esters, carbodiimides are the most commonly used. In a somewhat similiar process, molecules functionalized with phosphate groups, as for example, polynucleotide segments, can be activated by conversion to mixed sulfonic-phosphoric anhydrides, using any of many reagents well-known in the art.

Polysaccharides normally contain free alcohol groups. Many reagents are available that convert alcohol functions to intermediates that will in turn react facilely with amines, thiols, etc., thereby permitting a polysaccharide to be coupled to other molecules such as proteins. Examples of such alcohol-activating reagents are cyanogen bromide, 1,1'-carbonyldiimidazole, 2,2,2-trifluoroethanesulfonyl chloride, and 2-fluoro-1-methylpyridinium salts, to name a few.

In general, mild conditions are preferred for the conjugation. The pH should be in the range of about 3 to 11, preferably 5 to 9, specifically 7 to 8, temperature in the range of 0 to 60 C., preferably 20 to 25 C, and concentrations in the range of about $10^{-2}$ to $10^{-6}$M, preferably about $10^{-4}$M. It is preferred to link the two proteins of the conjugate using carbodiimide chemistry.

Solid Phase

The solid support, in the case of homogeneous and heterogeneous assay formats, can take many forms, including microtiter plates, microtiter strips, dipstick, beads of any size, glass or plastic tubes or wells, magnetic particles such as chromium dioxide, latex particles and porous membranes, to name a few.

Detection Means

The detection means for the assays can be, but is not restricted to, an enzyme, coenzyme, change in particle agglutination, chemiluminescence, bioluminescence, or radioisotope. Enzymes which can be used as labels include alkaline phosphatase, horseradish peroxidase, and betagalactosidase, to name a few.

Assay Formats

Many different immunoassay configurations can be utilized using a mixture of conjugated and unconjugated binding reagent. The specific composition of the mixture, or ratio, of conjugated to unconjugated binding reagent is dependent on the specific analyte, solid phase selected and format chosen for the given assay. This ratio can be determined by optimization with titration of conjugated binding reagent and unconjugated binding reagent utilized in coupling to the solid phase reagent. Either component may comprise as low as about 5% of the mixture of the coupling reagent, preferably 25% of the mixture and specifically about 50%. Some of the specific assay configurations are described here.

In a sandwich type assay mode, the mixture of conjugated and unconjugated binding reagent is attached to a solid support by any means available. This attachment can occur by passive adsorption or by specific chemical coupling. Covalent coupling can be through gluteraldehyde coupling, or reaction with heterobifunctional or homobifunctional coupling agents such as those supplied by Pierce, Rockford, Ill. The solid support is contacted with sample containing analytes to be measured or detected. These analytes will react with the solid phase, which comprises the mixture of conjugated and unconjugated binding reagent immobilized on the solid support, to form a complex. The solid phase can then be washed; however, this step is optional but preferred in cases where good sensitivity and specificity are desired. The complex of the analytes and solid phase is detected by contacting with the corresponding member of the binding pair which can be detected. If the sample is a human specimen and the analytes are antibodies, the detector conjugate will be composed of an anti-human Ig antibody linked to the detector. Standards and controls are treated in the same fashion as the sample specimen.

In yet another configuration of a sandwich assay, the mixture of conjugated and unconjugated binding reagent is immobilized on a solid phase. The solid phase is contacted with the specimen and allowed to react. After washing, if necessary due to sensitivity and specificity requirements, the solid phase is contacted with a means of detecting antibody. If the antibody captured from the specimen is of the Ig class, detectable Protein-A can be added. The Protein-A can be rendered detectable by conjugation to an enzyme or gold sol or other means.

This assay can also be performed in inhibition modes, competitive or blocking. By competitive mode is meant that the antibodies are simultaneously exposed to the sample containing analytes and the means of capture. By blocking mode is meant that the solid phase which is coated with the mixture of conjugated and unconjugated binding reagent is exposed to sample containing analyte, the solid phase complexes with analyte in the sample and is washed and the excess labeled analyte is added and binds to unoccupied sites on the solid phase.

The assay can be performed in a homogeneous mode, that is one which does not require a separation of the captured and free analyte before detection. The mixture of conjugated and unconjugated binding reagent is immobilized onto a high refractive index particle by covalent or adsorptive means. These particles are then contacted with the specimen. In the presence of antibody to the analyte, agglutination of the particles occurs. This agglutination can be detected visually, spectrophotometrically, by particle counting or nephelometrically.

In another homogeneous configuration, the mixture of conjugated and unconjugated binding reagent is immobilized onto the surface of the high refractive index particle as described above. This particle is contacted with the specimen. The mixture of the particle coated with the mixture of conjugated and unconjugated analyte and the analyte in the specimen is contacted with specific binding partner. This specific binding partner can be in solution or immobilized on the surface of a high refractive index particle. The immobilized mixture of conjugated and unconjugated analyte and the free analyte from the specimen compete for the binding sites of the antibody. Agglutination of the particles will occur. Contacting the particle, specimen, and specific binding partner can occur simultaneously or sequentially. In the absence of analyte in the specimen, the agglutination of the particles coated with the mixture of the conjugated and unconjugated analyte will be large. The presence of analyte from the specimen will inhibit this agglutination reaction. The presence or absence of analyte is determined in comparison to standards which are treated in the same manner as the sample specimen.

The following specific examples illustrate but do not limit the invention.

EXAMPLE 1

Improvement of Assay Performance Using The Mixture of Conjugated and Unconjugated Binding Reagent

A. Assay for Anti-HBc ELISA with rHBcAg solid phase

A competition format immunoassay for the detection of antibody directed against HBcAg was established according to the method of Adamich and Wos, U.S. Pat. No. 4,818,688, column 15, lines 12 through 42. The only exception to their protocol was the addition of 0.125% (w/v) Triton X-114 and 0.001M ethylenediaminetetraacetate (EDTA) to the solution that was used to dilute the enzyme-conjugated anti-HBc monoclonal antibody.

B. Anti-HBc ELISA with BSA-Conjugated rHBcAg Solid Phase

BSA was conjugated to recombinant Hepatitis B core antigen (rHBcAg) using the method described by Geerligs et al. for conjugation of BSA to rubella antigen. The amount of antigen contained in the conjugate was determined by comparison of dilution series of unconjugated and BSA-conjugated rHBcAg in an ELISA for the detection of rHBcAg. An ELISA was established that was identical to that described above except that BSA-conjugated rHBcAg was used as the solid phase reagent in place of rHBcAg. The amount of rHBcAg that was contained in the conjugate that was used to coat plates in this protocol was 250 ng/ml; the same as was used to coat plates as was used in the previous protocol.

C. Identification of False Positive Sample Populations

A group of 480 fresh normal donor sera was tested for the presence of anti-HBc antibody in both of the immunoassays described above. Also, a commercially available anti-HBc immunoassay (Organon-Technica HEPANOSTIKA(®) ANTICORE(TM)) was used as the reference method. Since there is no broadly accepted confirmatory method for anti-HBc testing, the reference method was considered to represent true positive or negative reactivity.

Eight of the samples yielded positive results in only one of the tests described in A or B above and negative results in the other two methods that were used. Since the only difference between the tests described in A and B is the unconjugated or BSA-conjugated nature of the solid phase reagent, these discrepant samples were referred to as rHBcAg-false positive and BSArHBcAg-false positive populations, respectively.

D. Anti-HBc ELISA with Mixture of Unconjugated and BSA-Conjugated rHBcAg Binding Reagent 1. Improvement in assay specificity.

Unconjugated and BSA-conjugated rHBcAg preparations are mixed in various proportions to a single final antigen concentration consistent with the solid phase reagent compositions described in Parts A and B. The antigen mixtures are contacted with the plates and allowed to react. The sera that were rHBcAg-false positive or BSArHBcAg-false positive as described above were tested using each combination of antigen forms.

As shown for each serum sample in Table 1, a and b, the level of false positivity brought about by one antigen form decreases as that antigen form is replaced by an equal concentration of the other antigen form. At equal antigen concentrations of each form, none of these samples is positive. Table 1, parts a and b present the same same information for purposes of clarity. In part a, results are expressed as direct experimental data; while part b is expressed as the ratio to the calculated cut-off of the assay. A separate cut-off value is determined for each antigen mixture as described in Adamich and Wos, U.S. Pat. No. 4,881,688, column 15, line 35–36.

TABLE 1

OPTIMIZATION OF THE COMPOSITION OF THE BINDING PHASE REAGENT

PART A: Experimental Data
SOLID PHASE ANTIGEN CONTENT:

| ng/mL rHBcAg =   | 250   | 187.5 | 125   | 62.5  | 0     |
| ng/mL BSArHBcAg = | 0     | 62.5  | 125   | 187.5 | 250   |
| Sample Number | Absorbance Value* | | | | |
| 220 | 0.267 | 0.319 | 0.416 | 0.383 | 0.501 |
| 320 | 0.343 | 0.313 | 0.462 | 0.411 | 0.539 |
| 342 | 0.233 | 0.327 | 0.463 | 0.495 | 0.783 |
| 351 | 0.224 | 0.284 | 0.445 | 0.532 | 0.814 |
| 376 | 0.439 | 0.420 | 0.503 | 0.589 | 0.799 |
| 221 | 0.784 | 0.568 | 0.475 | 0.263 | 0.154 |
| 340 | 1.035 | 0.815 | 0.595 | 0.331 | 0.252 |
| 395 | 1.085 | 0.817 | 0.667 | 0.348 | 0.303 |
| x Neg. Control (n = 3) | 1.883 | 1.553 | 1.307 | 1.130 | 1.495 |
| Assay cutoff (.25 × NC) | 0.470 | 0.388 | 0.327 | 0.283 | 0.374 |

*Absorbance @ 492 nm of final result of anti-HBc ELISA.

PART B: EXPERIMENTAL DATA EXPRESSED AS RATIO TO ASSAY CUT-OFF
SOLID PHASE ANTIGEN CONTENT:

| ng/mL rHBcAg =   | 250  | 187.5 | 125  | 62.5 | 0    |
| ng/mL BSArHBcAg = | 0    | 62.5  | 125  | 187.5 | 250  |
| Sample Number | Absorbance Value* | | | | |
| 220 | 0.57 | 0.82 | 1.27 | 1.35 | 1.34 |
| 320 | 0.73 | 0.81 | 1.32 | 1.45 | 1.44 |
| 342 | 0.49 | 0.84 | 1.42 | 1.75 | 2.09 |
| 351 | 0.48 | 0.73 | 1.36 | 1.88 | 2.18 |
| 376 | 0.93 | 1.08 | 1.54 | 2.08 | 2.11 |
| 221 | 1.66 | 1.46 | 1.45 | 0.93 | 0.41 |
| 340 | 2.20 | 2.10 | 1.82 | 1.17 | 0.67 |
| 395 | 2.30 | 2.11 | 2.04 | 1.23 | 0.81 |

*RTCo = Ratio to calculated cutoff of anti-HBc ELISA = value of calibrated negative control × 0.25. A negative control sample was included for each antigen mixture. Since this is a competition format assay, RTCo values of less than 1.0 indicate that the sample was positive for anti-HBc.

2. Improvement in assay sensitivity.

A doubling dilution series of a known anti-HBc positive serum was prepared in a known anti-HBc negative serum. The dilution series was tested in anti-HBc ELISA with the solid phase being constructed of rHBcAg, BSArHBcAg or an equal mixture of rHBcAg and BSArHBcAg as described above. Table 2 shows that with the mixed antigen solid phase, the dilutional titer was higher than with either the rHBcAg or the BSA-conjugated rHBcAg solid phase. Again, the data is presented as raw experimental data and as ratio to cutoff, for purposes of clarity.

Part A: EXPERIMENTAL DATA

| Dilution of positive serum | (Absorbance) | | |
| --- | --- | --- | --- |
| | rHBcAg | BSA-rHBcAg | rHBcAg + BSA-rHBcAg |
| 1:8 | 0. | 0.017 | 0.002 |
| 1:16 | 0.004 | 0.045 | 0.005 |
| 1:32 | 0.029 | 0.154 | 0.019 |
| 1:64 | 0.160 | 0.373 | 0.070 |
| 1:128 | 0.787 | 0.666 | 0.223 |
| 1:256 | 1.323 | 1.050 | 0.458 |
| 1:512 | 1.644 | 1.461 | 0.855 |
| 1:1024 | 1.703 | 1.545 | 1.046 |
| x Neg. Control | 2.020 | 1.628 | 1.468 |
| Assay cutoff (.25 × NC) | 0.505 | 0.407 | 0.367 |
| end point · titer = | 1:64 | 1:64 | 1:128 |

*Abs. = Absorbance @ 450 mm of final result of anti-HBc ELISA.

PART B: Anti-HBc ELISA: COMPARISON OF SOLID PHASE REAGENTS FOR ASSAY SENSITIVITY.

| Dilution of positive serum | Ratio to cutoff* | | |
| --- | --- | --- | --- |
| | rHBcAg | BSA-rHBcAg | rHBcAg + BSA-rHBcAg |
| 1:8 | 0. | 0.04 | 0.01 |
| 1:16 | 0.01 | 0.11 | 0.01 |
| 1:32 | 0.06 | 0.38 | 0.05 |
| 1:64 | 0.32 | 0.92 | 0.19 |
| 1:128 | 1.56 | 1.64 | 0.61 |
| 1:256 | 2.61 | 2.58 | 1.25 |
| 1:512 | 3.25 | 3.59 | 2.33 |
| 1:1024 | 3.37 | 3.80 | 2.85 |
| end point titer = | 1:64 | 1:64 | 1:128 |

*RTCo = Ratio to calculated cutoff of anti-HBc ELISA = value of calibrated negative control × 0.25. A negative control sample was included for each antigen mixture. Since this is a competition format assay, RTCo values of less than 1.0 indicate that the sample was positive for anti-HBc.

I claim:

1. A solid phase heterogeneous or homogeneous immunoassay to detect or quantitate an analyte in a liquid sample which comprises:
   a) reacting binding reagent, immobilized on a solid phase, with sample; and
   b) determining the extent of binding which occurs in step (a);
   wherein the immobilized binding reagent is a mixture of carrier-conjugated and unconjugated binding reagent in which the ratio of carrier-conjugated binding reagent to unconjugated binding reagent is in the range from 1:19 to 19:1.

2. An immunoassay of claim 1 wherein the analyte and binding reagent are members of an immunochemical binding pair.

3. Immunoassay of claim 2 wherein the carrier is a protein selected from bovine serum albumin, human serum albumin, ovalbumin, gelatin and casein.

4. Immunoassay of claim 3 wherein said assay is a competition immunoassay and further wherein the immobilized mixture of carrier protein-conjugated binding reagent and unconjugated binding reagent is contacted with sample and with labeled analyte, then reagents are added to determine the extent of binding of the immobilized binding reagent to labeled analyte.

5. Competition immunoassay of claim 4 wherein the binding reagent is a mixture of conjugated and unconjugated rHBcAg, the analyte is anti-HBc antibody, and the labeled analyte is enzyme-labeled high affinity monoclonal anti-HBc antibody.

6. Sandwich immunoassay of claim 1 wherein the immobilized binding reagent is contacted with a liquid sample, then reagents are added to determine the extent of binding of the immobilized binding reagent to the analyte.

7. Agglutination assay of claim 1 wherein a binding reagent which selectively binds the analyte is immobilized on the surface of a high refractive index particle and the immobilized binding reagent is contacted with a liquid sample and with a reagent which selectively binds the analyte, then the extent of agglutination of the immobilized binding reagent is determined.

8. Inhibition of agglutination assay of claim 1 wherein a binding reagent which selectively binds a reagent which selectively binds the analyte is immobilized on the surface of a high refractive index particle and the immobilized binding reagent is contacted with a liquid sample and with the reagent which selectively binds the analyte, then the extent of agglutination of the immobilized binding reagent is determined.

9. Agglutination assay of claim 8 wherein the binding reagent is the same as the analyte or is an analog of the analyte.

10. An immunoassay according to claim 1 wherein the reacting binding reagent in step (a) is immobilized directly on the solid phase.

11. An immunoassay according to claim 1 wherein the binding reagent in step (a) is immobilized through an intermediate on the solid phase.

12. An immunoassay according to claims 10 or 11 wherein another reagent which selectively binds the analyte is additionally reacted with the binding reagent.

13. An immunoassay according to claims 10, 11 or 12 wherein a labeled analyte is additionally reacted with the binding reagent.

14. An immunoassay according to claim 1 wherein the immobilized binding reagent is a mixture of carrier-conjugated and unconjugated binding reagent in which the ratio of carrier-conjugated binding reagent to unconjugated binding reagent is in the range from 1:3 to 3:1.

15. An immunoassay according to claim 1 wherein the immobilized binding reagent is a mixture of carrier-conjugated and unconjugated binding reagent in which the ratio of carrier-conjugated binding reagent to unconjugated binding reagent is in the range from 2:3 to 3:2.

* * * * *